United States Patent [19]

Saice

[11] 3,970,089

[45] July 20, 1976

[54] CARDIOVASCULAR CATHETER SEAL DEVICE

[76] Inventor: Dwayne D. Saice, 1800 Rose Glen Ave., San Pedro, Calif. 94931

[22] Filed: Aug. 5, 1974

[21] Appl. No.: 494,463

[52] U.S. Cl. .............................. 128/348; 128/325; 277/34.3
[51] Int. Cl.² ...................................... A61M 25/00
[58] Field of Search ......................... 128/348–351, 128/344, 325, 246, 1 R; 277/34, 34.3

[56] References Cited
UNITED STATES PATENTS

| | | | |
|---|---|---|---|
| 2,841,422 | 7/1958 | Badger | 277/34 |
| 3,339,011 | 8/1967 | Ewers et al. | 277/34 X |
| 3,402,710 | 9/1968 | Paleschuck | 128/1 R |
| 3,471,156 | 10/1969 | Burns et al. | 277/34 X |
| 3,797,478 | 3/1974 | Walsh et al. | 128/1 R |

*Primary Examiner*—Dalton L. Truluck
*Attorney, Agent, or Firm*—Lyon & Lyon

[57] ABSTRACT

A device capable of sealing the extracorporeal end of a catheter sheath in which has been disposed a catheter is described. An elastomeric member such as a toroidal bladder is confined within a chamber defined by a rigid, hollow body portion and controllably distended so as to restrict a lumen through which the catheter passes, thus effecting a seal against the egress of blood in course of catheterization. Means are provided to permit the admission of fluids or withdrawal of blood samples, etc. at the proximal end of the catheter sheath simultaneously with catheterization.

9 Claims, 3 Drawing Figures

U.S. Patent   July 20, 1976   3,970,089
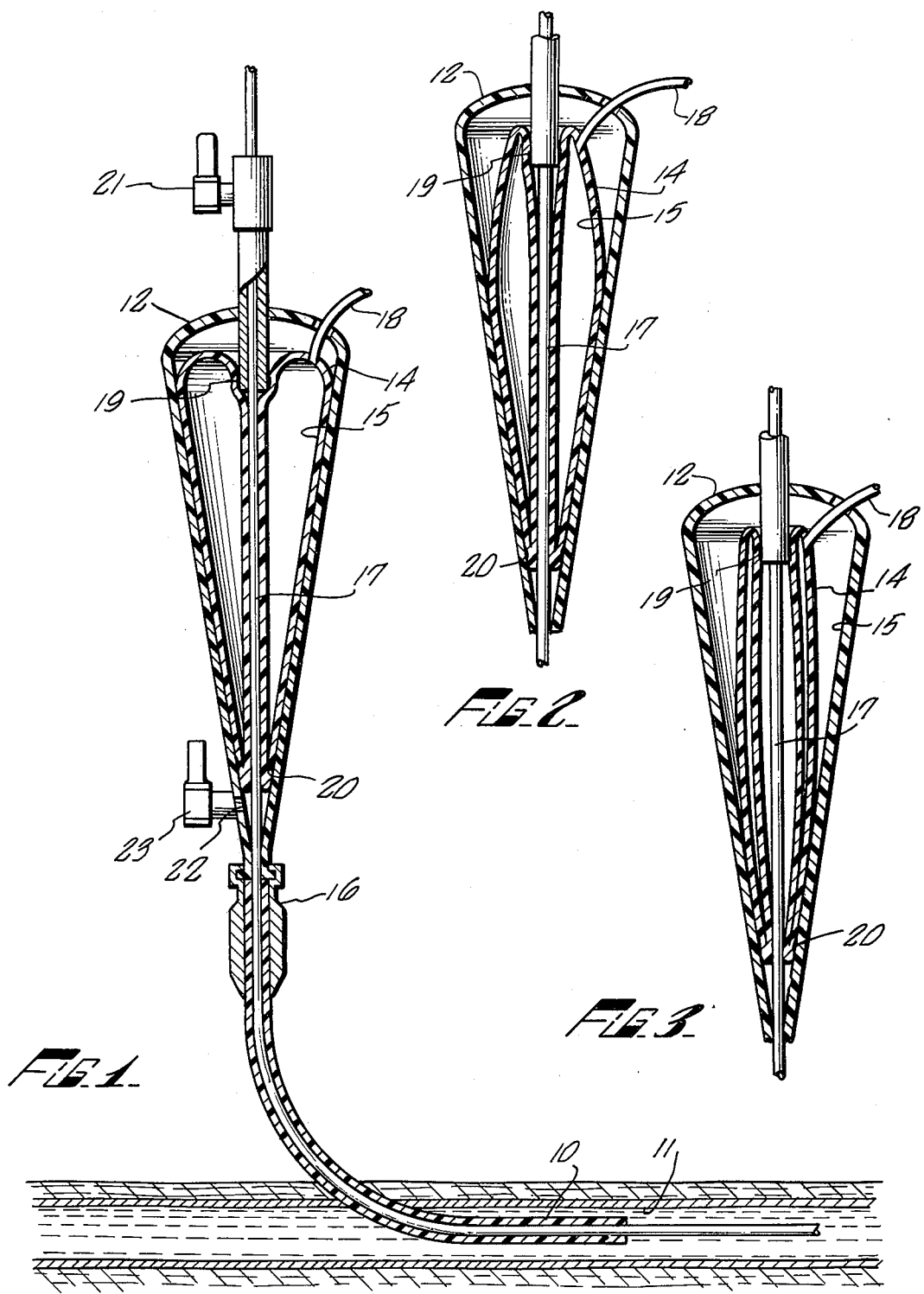

CARDIOVASCULAR CATHETER SEAL DEVICE

BACKGROUND OF THE INVENTION

This invention relates to catheterization practice, and more particularly to means by which a sheath through which a catheter is passed may be controllably sealed.

Catheterization, as that term is used herein, implies the passage of an elongate, usually hollow member, into and along vessels of the cardiovascular system. Catheters are widely employed in measurement of vascular pressures, angiography, blood gas determinations, indicator dilution studies and the like. Percutaneous techniques of catheter placement have become increasingly popular, replacing to a significant extent procedures requiring exposure of the vessel by surgical cutdown. In the so-called "Seldinger" percutaneous technique, the vessel wall and overlying tissue is pierced with a hollow needle through which a flexible wire is passed into the vessel. The needle is withdrawn over the extracorporeal end of the wire, which is then used to guide a relatively stiff catheter introducer or vessel dilator bearing a catheter sheath into the vessel. Once the sheath is in place, both introducer and wire are withdrawn, and the extracorporeal or distal end of the sheath is sealed, as with a luer lock seal, pending introduction of a catheter through the sheath. This technique has proved generally satisfactory for venous catheterizations, notwithstanding the fact that when a catheter is passed through the distal end of the sheath a leak path invariably is created along the sheath-catheter interface, owing to the relatively low vascular pressures encountered in such catheterizations. To the extent they permitted introduction of anticoagulants such as heparin only at the proximal end of the catheter, catheterization techniques heretofore in use were more likely subject to coltting adjacent the point of catheter entry. Again, such clotting is of but minor concern in venous catheterization, since transmigrating clots tend to be filtered in the lungs without any adverse effect. But in arterial catheterization, uncontrolled clotting can lead to major vascular and coronary occlusions. For that reason and because of the great vascular pressures which are exerted along the sheath-catheter interface with the concomitant risk of substantial blood loss, arterial catheterization has until now been less widely practiced and more commonly problematic than venous catherization. In view of the importance of the former in, e.g., aortic arch and branch radiography, renal studies, studies of the left heart and of the vascular anatomy of the brain, it is apparent that a need exists for improved catheter sheath sealing means, and particularly for such means safely suited to arterial catheterization techniques.

BRIEF SUMMARY OF THE INVENTION

According to this invention there is provided a cardiovascular catheter seal device adapted to adjustably seal the extracorporeal or distal end of an emplaced catheter sheath. A catheter may be passed through the device, and into and through a sheath affixed to its proximal end. The device comprises a hollow rigid body defining a chamber which contains an elastomeric member having a lumen through which the catheter is passed. By distending the elastomeric member to constrict the lumen, a seal against egress of blood along the interface between catheter and the innermost surface of the member is effected. In preferred embodiments, ancillary means permit addition of or withdrawal of fluids at the proximal end of the sheath, and sealing after the catheter has been withdrawn from the sheath.

The manner in which these and other objects and advantages of the invention are achieved will become apparent from the detailed description which follows, and from the accompanying drawing of a preferred embodiment, in which like reference numerals indicate like elements and in which:

FIG. 1 illustrates, in partial cross-section, the manner in which the device is employed to seal a catheter which has been passed through a sheath and into an arterial vessel; and FIGS. 2 and 3 respectively illustrate progressive relaxation of the elastomeric member employed to effect the full seal depicted in FIG. 1.

DETAILED DESCRIPTION OF THE INVENTION

FIG. 1 depicts a catheterization in progress, a catheter sheath 10 having been passed, as by the aforementioned Seldinger technique, through overlying tissue into an arterial vessel 11. To the distal end of the sheath 10 has been affixed a preferred cardiovascular catheter seal device having a hollow, rigid body 12 whose interior walls 13 define a chamber open at its proximal and distal ends. Within the chamber is a thin-walled elastomeric member 14. As most clearly appears from FIG. 3, the innermost surface 15 of elastomeric member 14 defines a lumen in communication with the openings at the proximal and distal ends of the chamber defined by the walls of body portion 12. Means such as luer fitting 16 are provided adjacent to the proximal end of the catheter seal device for affixation of the catheter sheath 10 in registry with the aforesaid lumen. The sheath, lumen and proximal end distal openings in the catheter seal chamber accordingly define a passageway through which may be passed catheter 17. Elastomeric member 14 may be progressively distended, as shown in FIGS. 2 and 1, so as to constrict the lumen defined by its innermost surface, sealing the interface between that surface and the catheter against the passage of blood. In preferred embodiments like that depicted in the drawing, the elastomeric member is a toroidal bladder, preferably provided with means such as flexible conduit 18 by which adjustably variable quantities of air or other inflating fluid can be admitted to the bladder, occasioning its distension into sealing engagement with the catheter. Alternatively, albeit less desirably, distension of the elastomeric member could be effected by other means, e.g., evacuation of the chamber in which it is contained, so as to occasion expansion of a gas contained within the bladder, etc. Again, rather than the toroidal bladder depicted in the drawing, the elastomeric member may assume the form of a cylindrical sleeve sealed to the body portion at its opposite ends so as to admit of radially inward distension by the agency of a gas admitted through the body portion 12 at a point intermediate the sealed ends of the sleeve.

In any event, the elastomeric member is secured within the chamber so as to prevent passage of blood through the chamber exteriorly of the lumen during catheterization. In the device illustrated in the drawing, that object is attained by effecting bonds 19 and 20 respectively between member 14 and portions of body 12 adjacent the openings at its distal and proximal ends. With the non-pyrogenic natural latex elastomeric member and polycarbonate body preferred in the practice of this invention, conventional epoxy cement is suitable in effecting such bonds.

Preferably, the distal end of the catheter seal device is provided with valving means, such as stopcock 21, by which the device may be sealed against the passage of blood therethrough prior to insertion of the catheter or following its withdrawal.

The operation of the device as thus far described is as follows. A catheter sheath is conventionally emplaced in an arterial or other vessel and the catheter seal device affixed to its extracorporeal end. Pending the insertion of a catheter, stopcock 21 may be employed to prevent egress of blood through the device. When a catheter has been passed through the lumen defined by elastomeric member 14, that member is partially distended as in FIG. 2. At this stage, dog studies with the depicted device have demonstrated that the pressure exerted at the elastomeric member-catheter interface is quite sufficient to prevent any leakage of arterial blood, but insufficient to impede the movement of the catheter through the catheter seal device. Once the catheter has been advanced through the seal device-catheter sheath assembly to a desired extent, the elastomer member is fully distended. Thereafter, until member 14 is relaxed, catheter 17 is immovably held by engagement therewith. To withdraw the catheter, member 14 is permitted to relax, as to the extent shown in FIG. 2, whereupon the catheter can be withdrawn while yet preventing blood loss.

Preferably, the catheter seal device is provided with an additional opening 22 adjacent the proximal end of the chamber and in communication therewith at a point intermediate with the proximal ends of elastomeric member 14 and of the chamber defined by surface 13. Valving means 23 associated with that opening permit controlled egress and ingress of fluids therethrough. Means 23 can accordingly be used to withdraw blood samples and to admit intravascular medications, radio-opaque contrast media and the like during catheterization. Means 23 can also be employed to admit flushing agents such as heparinized saline to the vessel from the proximal tip of the catheter sheath, irrespective of the catheter tip locus. Means 23 also permits hemodynamic evaluation calculated to determine, e.g., cardiac output by indicator dilution procedures. Characteristically in the course of such evaluations, a measured quantity of a detectable dye or other indicator is passed from the catheter tip into a vascular chamber and, at a set time thereafter, blood sampling at a point distant from the catheter tip is commenced. Heretofore, it has been necessary in such evaluation to subject the patient to a further invasive procedure at the point at which sampling is to be effected, with concomitant prolongation of the procedure and risk of traumatization.

From the foregoing, it will be seen that this invention provides versatile means for effecting seals during catheter insertion, use and removal, and permits to a degree heretofore never obtained safe and convenient emplacement and use of arterial catheters. The catheter seal device is suitable for use with essentially any catheter, including blood gas electrode catheters, angiographic catheters, tip transducers, non-end hole catheters, etc.

Having described my invention principally by reference to the preferred embodiments thereof, I wish it understood that I am not bound therby, but only by the lawful scope accorded the claims which next follow.

I claim:
1. A cardiovascular catheter seal device comprising:
A hollow rigid body whose interior walls define a chamber open at its proximal and distal ends for the passage of a catheter therethrough;
within said chamber, a thin-walled elastomeric member whose innermost surface defines a lumen in communication with said openings so as to receive and pass said catheter, said member being secured within said body so as to prevent passage of blood through the chamber exteriorly of said lumen during catheterization;
means to adjustably distend the innermost surface of said member radially inwardly to constrict said lumen, sealing the interface between said surface and a catheter received in the lumen against the passage of blood therealong; and
catheter sheath attachment means adjacent the proximal end of said device said attachment means being a luer fitting.

2. A catheter seal device according to claim 1 which additionally comprises valving means to seal said chamber against the passage of blood therethrough absent said catheter.

3. A device according to claim 1 wherein said chamber diminishes in its lateral dimension progressively from a point adjacent the distal end to a point adjacent the proximal end thereof.

4. A cardiovascular catheter seal device comprising:
A hollow rigid body whose interior walls define a chamber open at its proximal and distal ends for the passage of a catheter therethrough;
within said chamber, a thin-walled elastomeric member whose innermost surface defines a lumen in communication with said openings so as to receive and pass said catheter, said member being secured within said body so as to prevent passage of blood through the chamber exteriorly of said lumen during catheterization:
means to adjustably distend the innermost surface of said member radially inwardly to constrict said lumen, sealing the interface between said surface and a catheter received in the lumen against the passage of blood therealong;
catheter sheath attachment means adjacent the proximal end of said device; and
an additional opening adjacent the proximal end of said chamber in communication therewith at a point intermediate said attachment means and the proximal end of said member, and valving means associated with said additional opening to controllably permit ingress and egress of fluids therethrough and through the proximal end of said device when said interface is sealed.

5. A cardiovascular catheter seal device comprising:
a. a hollow rigid body whose interior walls define a chamber open at its proximal and distal ends for the passage of a catheter therethrough;
b. within said chamber, a thin-walled elastomeric member whose innermost surface defines a lumen in communication with said openings so as to receive and pass said catheter, said member being secured within said body so as to prevent passage of blood through the chamber exteriorly of said lumen during catheterization;
c. means to adjustably distend the innermost surface of said member inwardly to constrict said lumen, sealing the interface between said surface and a catheter received in the lumen against the passage of blood therealong;

d. catheter sheath attachment means adjacent the proximal end of said device; and e. a catheter sheath affixed adjacent the proximal end of said body in registry with said lumen.

6. An assembly comprising the device of claim 5 and a catheter occupying the passageway defined by the sheath, proximal opening, lumen and distal opening of said device.

7. A device according to claim 5 wherein said elastomeric member is a toroidal bladder.

8. A device according to claim 7 wherein the means (c) permit adjustable distension of said bladder by the passage of an inflating fluid into it, said device having an additional opening adjacent the proximal end of said chamber in communication therewith at a point intermediate the proximal ends of said body and member, and valving means associated with said additional opening to controllably permit ingress and egress of fluids therethrough and through the proximal end of said device when said interface is sealed.

9. An assembly comprising a. a catheter seal device according to claim 8; and b. a catheter occupying the passageway defined by said sheath, proximal opening, lumen and distal opening.

* * * * *